(12) United States Patent
Bresina et al.

(10) Patent No.: US 10,912,639 B2
(45) Date of Patent: Feb. 9, 2021

(54) IMPLANT SYSTEM FOR REPAIR OR REPLACEMENT OF TENSION CARRYING CONNECTIVE TISSUE

(71) Applicant: KYON AG, Zürich (CH)

(72) Inventors: Stephen Bresina, Davos Dorf (CH); Slobodan Tepic, Zurich (CH)

(73) Assignee: Kyon AG, Zürich (CH)

( * ) Notice: Subject to any disclaimer, the term of this patent is extended or adjusted under 35 U.S.C. 154(b) by 71 days.

(21) Appl. No.: 16/095,096

(22) PCT Filed: Apr. 21, 2017

(86) PCT No.: PCT/EP2017/059510
§ 371 (c)(1),
(2) Date: Oct. 19, 2018

(87) PCT Pub. No.: WO2017/182624
PCT Pub. Date: Oct. 26, 2017

(65) Prior Publication Data
US 2019/0117376 A1    Apr. 25, 2019

(30) Foreign Application Priority Data

Apr. 22, 2016 (EP) ..................... 16166610

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61B 17/0466* (2013.01); *A61B 17/0487* (2013.01); *A61F 2/08* (2013.01); *A61F 2/3836* (2013.01); *A61B 2017/044* (2013.01); *A61B 2017/0445* (2013.01);
(Continued)

(58) Field of Classification Search
CPC ........ A61F 2/0811; A61F 2/08; A61F 2/3836; A61F 2002/0829; A61F 2002/0852; A61F 2002/0864; A61F 2002/087; A61F 2002/0888; A61F 2002/30461;
(Continued)

(56) References Cited

U.S. PATENT DOCUMENTS 5,108,433 A    4/1992 May et al.
6,148,597 A    11/2000 Cook
(Continued)

FOREIGN PATENT DOCUMENTS

EP    0 260 787 A1    3/1988

OTHER PUBLICATIONS

Anonymous: "Joint Stabilization System (Ruby)", KYON Veterinary Surgical Products, Jan. 1, 2015, Retrieved from the Internet: 5 pages.
(Continued)

*Primary Examiner* — Suba Ganesan
*Assistant Examiner* — Aren Patel
(74) *Attorney, Agent, or Firm* — Rothwell, Figg, Ernst & Manbeck, P.C.

(57) ABSTRACT

A link (1) for connecting two loops of a flexible tension-carrying construct (2, 2a). It solves the problem of providing effective means to connect two anchor points (7, 7a), typically on bones articulating at a joint by the flexible tension-carrying construct.

12 Claims, 9 Drawing Sheets

Figure 1:
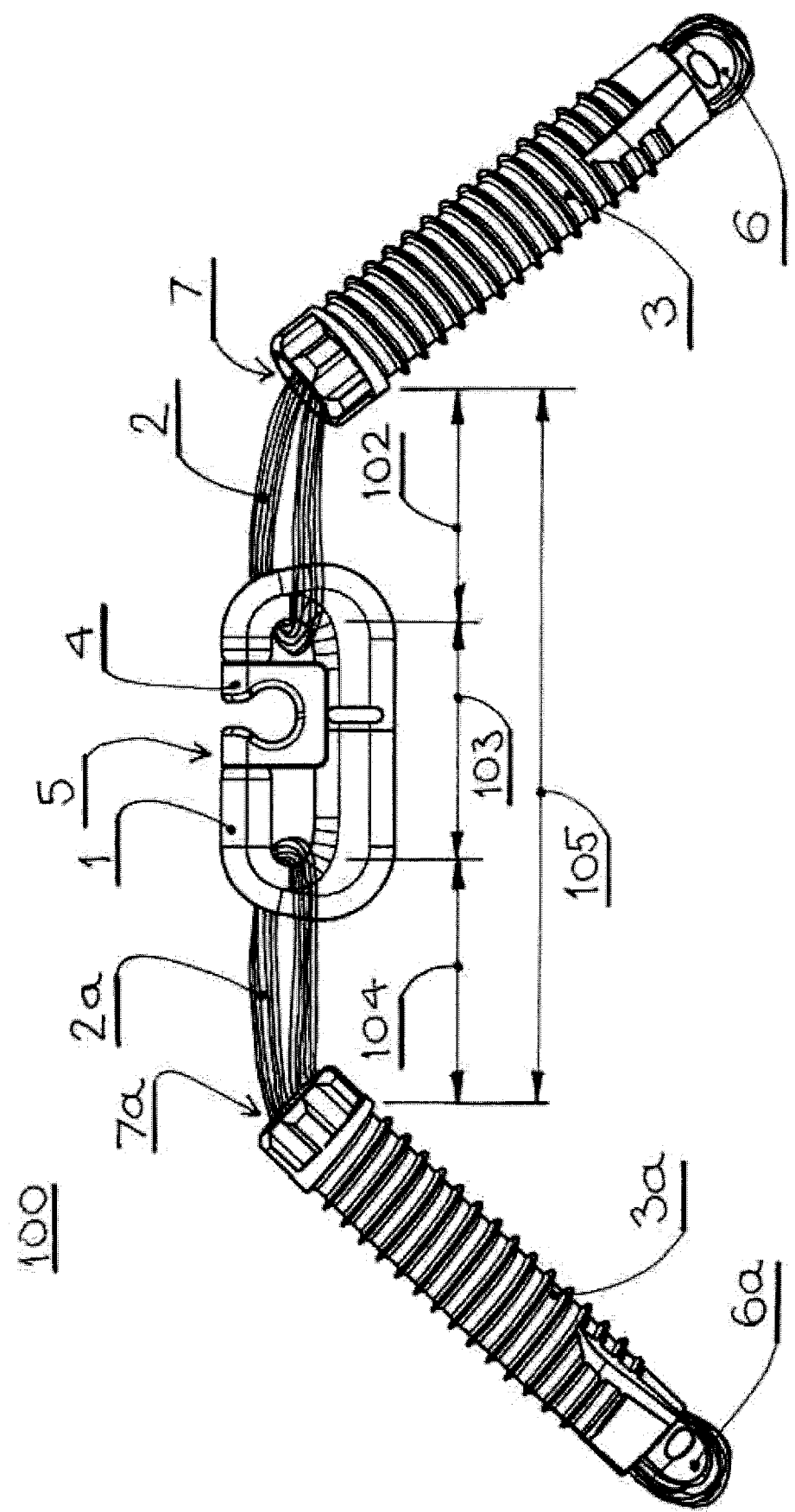

(51) Int. Cl.
    *A61F 2/38*           (2006.01)
    *A61F 2/30*           (2006.01)

(52) U.S. Cl.
    CPC . *A61B 2017/0451* (2013.01); *A61F 2002/087* (2013.01); *A61F 2002/0829* (2013.01); *A61F 2002/0852* (2013.01); *A61F 2002/0864* (2013.01); *A61F 2002/0888* (2013.01); *A61F 2002/307* (2013.01); *A61F 2002/3085* (2013.01); *A61F 2002/30461* (2013.01); *A61F 2250/0081* (2013.01)

(58) Field of Classification Search
    CPC ........ A61F 2002/307; A61F 2002/3085; A61F 2250/0081; A61B 17/0401; A61B 17/0466
    USPC ...................................................... 623/13.12
    See application file for complete search history.

(56) References Cited

U.S. PATENT DOCUMENTS

| | | |
|---|---|---|
| 8,721,684 B2 | 5/2014 | Denham et al. |
| 2008/0195148 A1 | 8/2008 | Cook et al. |
| 2011/0319994 A1 | 12/2011 | Tepic et al. |
| 2012/0089193 A1 | 4/2012 | Stone et al. |
| 2013/0023928 A1* | 1/2013 | Dreyfuss ............ A61B 17/0401 606/228 |
| 2015/0018881 A1* | 1/2015 | Cauldwell ............ A61F 2/0811 606/232 |
| 2015/0073475 A1* | 3/2015 | Schaller ................ A61F 2/0811 606/232 |
| 2015/0141995 A1* | 5/2015 | Norton ................ A61B 17/823 606/74 |
| 2015/0289866 A1* | 10/2015 | Bowen ................ A61F 2/0811 606/232 |
| 2016/0120639 A1* | 5/2016 | Murray ................ A61F 2/389 623/13.12 |

OTHER PUBLICATIONS

International Search Report cited in PCT/EP2017/059510, dated Sep. 13, 2017, 5 pages.

* cited by examiner

IMPLANT SYSTEM FOR REPAIR OR REPLACEMENT OF TENSION CARRYING CONNECTIVE TISSUE

CROSS REFERENCE TO RELATED APPLICATION

This application is a 35 U.S.C. 371 National Phase Entry Application from PCT/EP2017/059510, filed Apr. 21, 2017, which claims the benefit of European Patent Application No. 16166610.2 filed on Apr. 22, 2016, the disclosures of which are incorporated herein in their entirety by reference.

FIELD OF THE INVENTION

This invention solves the problem of providing effective means to connect two anchor points, typically, but not necessarily, on bones articulating at a joint by a flexible tension-carrying construct.

Utility of high strength materials, such as highly oriented ultra-high molecular weight polyethylene for repair or replacement of damaged or ruptured ligaments and tendons is greatly limited by the problems of tying reliable knots or using crimping means of different designs. The fundamental limitation comes from the very low friction of these materials as well as from introduction of high stresses at the point of knotting or crimping.

This invention circumvents the need to tie knots or use crimping means, bringing the ultimate strength of the construct closer to the theoretical limit of the materials.

BACKGROUND

Frequently encountered problems in trauma and orthopedic surgery relate to affixing damaged or ruptured soft tissues, such as ligaments and tendons to hard bone tissue. When fixing ligament-to-ligament, or bone-to-bone, surgeons rely on using appropriate means, e.g. sutures for repair of soft tissues and plates and screws for mending broken bones. However, when soft tissue needs to be attached directly to bone, or when a ligament across a joint is to be replaced, choices become less clear.

The preferred method of attaching a tension element, which in this text we will refer to as a suture, to a bone is via a bone anchor. A refined version of a bone anchor is disclosed in the US patent application 2011/0319994 by Tepic et al. It comprises a bone anchor screw, preferably manufactured from titanium or a titanium alloy, a ruby eyelet at the exit side of the anchor and a grooved conical pin to affix a loop of the suture to the anchor.

State of the art sutures are usually placed through bone tunnels, which inevitably leads to bone resorption and abrasion of the suture at the edges of the bone tunnels. An example of such a system is described in the US patent application 2008/0195148 by Cook et al. Early mechanical failures of such sutures are inevitable. Inflammation and infection of bone and peri-articular tissue due to constant motion of the suture in the bone tunnel are frequent clinical complications. Application of these extracapsular lateral sutures also involves tying of the knots or use of crimping techniques to fix the needed length of the suture between the anchor points. Neither of these techniques is suitable for securing ultra-high molecular weight polyethylene sutures, so most of the marketed sutures are produced with a jacket of less slippery, but also weaker fibers such as polyester, which is not only weaker but also more prone to abrasion against bone.

SUMMARY OF THE INVENTION

According to the present invention, the draw-backs of the prior art are overcome by providing a tension-carrying implant in the shape of an open link. The implant is suitable for securing at least one closed loop of suture-type material, particularly for connecting at least two closed loops of suture-type material. The implant may additionally comprise further elements, e.g. a link lock for closing the opening in the implant. The implant may be provided in a desired length or, preferably, in a set of desired different lengths. The implant may be produced from biocompatible materials such as metals, ceramics or combinations thereof. Preferred materials are titanium or titanium alloys, stainless steels, cobalt-chromium alloys or ceramics including mono-crystalline ceramics such as ruby, but also polycrystalline ceramics have found to be suitable.

The implant may be provided as a component of a tension-carrying construct which comprises at least one closed loop of suture-type material which is secured to the implant. The construct may additionally comprise at least one anchor element, e.g. one anchor element or two anchor elements. The anchor elements may be formed as bone anchors and/or as anchors to tendons or ligaments. The anchor elements may have a tubular form with a hollow interior, e.g. a central axial hole, through which a closed loop of suture material extends. The anchor elements and the closed loop of suture-type material may be preassembled into a loop-anchor implant with a first free length of the loop proximal to the link for insertion therein and a second free length distal to the link for anchoring to a bone or another physiological structure, e.g. a tendon or ligament. The loop-anchor implant may also comprise securing means for the closed loop of suture material distal to the link, e.g. a grooved peg inserted between the anchor element, e.g. the bone anchor, and the anchored end of the closed loop.

In an embodiment of the invention, the anchor element is provided with an abrasion-reducing eyelet, e.g. a eyelet made from a suitable ceramic, e.g. ruby.

The closed loops of suture material are preferably free from knots and/or crimps. They may be produced by multiple folding of a loop produced from a single yarn length which may be air-spliced or tied end-to-end to close the loop. The material of the loop is a polymeric fiber, e.g. a polyethylene fiber such as ultra-high molecular weight polyethylene. The fibers for the loops may be fused together, e.g. at a temperature between about 140° C. and about 160° C., preferably between about 147° C. and about 153° C., and more preferably between about 149° C. and about 151° C. The fusion of the fibers of the loop may be carried out with the addition of fusion aid, e.g. an oil or α-tocopherol, a form of vitamin E, including derivatives thereof.

In an embodiment of the invention, the construct may comprise two bone anchors with the first free lengths of the two loops plus the length of the link adding to a total length matching the desired distance between the both bone anchors.

In a preferred embodiment of the invention, two such bone anchors with preassembled suture loops of pre-measured lengths are inserted into bones at the desired locations, leaving a small gap between the two suture loops, whose added lengths are somewhat shorter when compared to the distance between the anchor points. The assembly is then completed by use of an open link that is hooked through the respective closed loops of the two sutures. The link is then secured from slipping out from either suture loop by a snap-in locking element, a link lock. Fine-tuning of the overall length of the suture can be accomplished by providing link elements in small length increments.

The construct according to the present invention may be used in human or veterinary medicine, e.g. as a lateral, extra-capsular suture in animals, e.g. in dogs with cranial cruciate deficiency.

A relevant and beneficial application of this system is for stabilization of a canine knee joint with a ruptured cranial cruciate ligament, wherein the bone anchors are placed at appropriate positions on the lateral aspect of the joint, one into the femur and one into the tibia, approximately at so-called isometric points.

In a further aspect, the present invention relates to a construct comprising at least one bone anchor with a closed suture loop, a link and a link lock used to affix a torn tendon to bone by means of multiple strands of a suture material.

In a still further aspect, the present invention refers to a process of fusing polyethylene fibers, particularly UHMWPE fibers, wherein the process is facilitated by addition of α-tocopherol, a form of vitamin E, including derivatives thereof carried out at between about 140° C. and about 160° C., preferably between about 147° C. and about 153° C., and more preferably between about 149° C. and about 151° C.

LIST OF FIGURES

FIG. 1 An assembly of a construct with two bone anchors including corresponding suture loops plus a link and a link lock.

Figure 2:
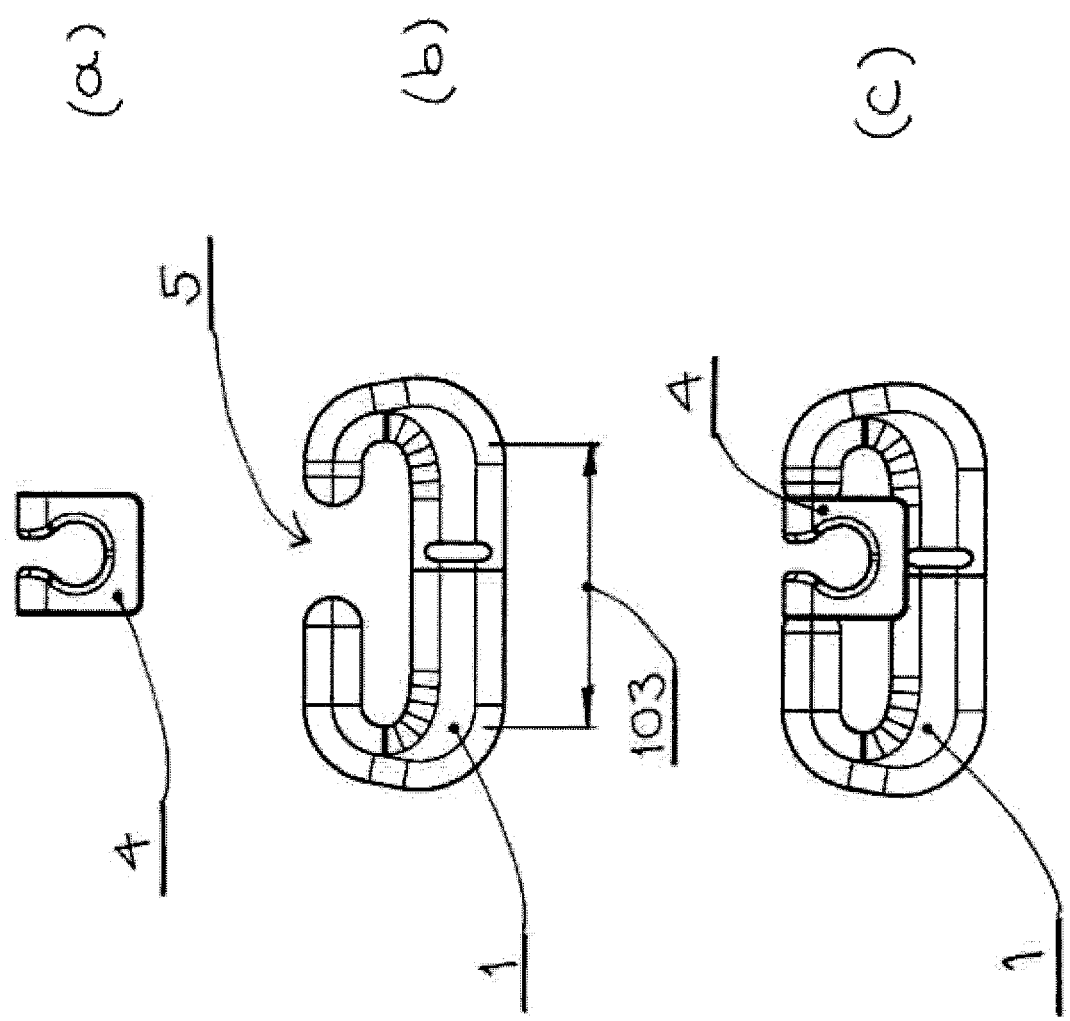

FIG. 2 A link with a link lock.

Figure 3:
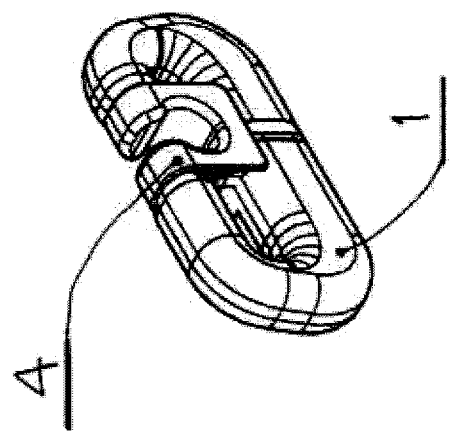

FIG. 3 A perspective view of a link and the link lock snapped in place.

Figure 4:
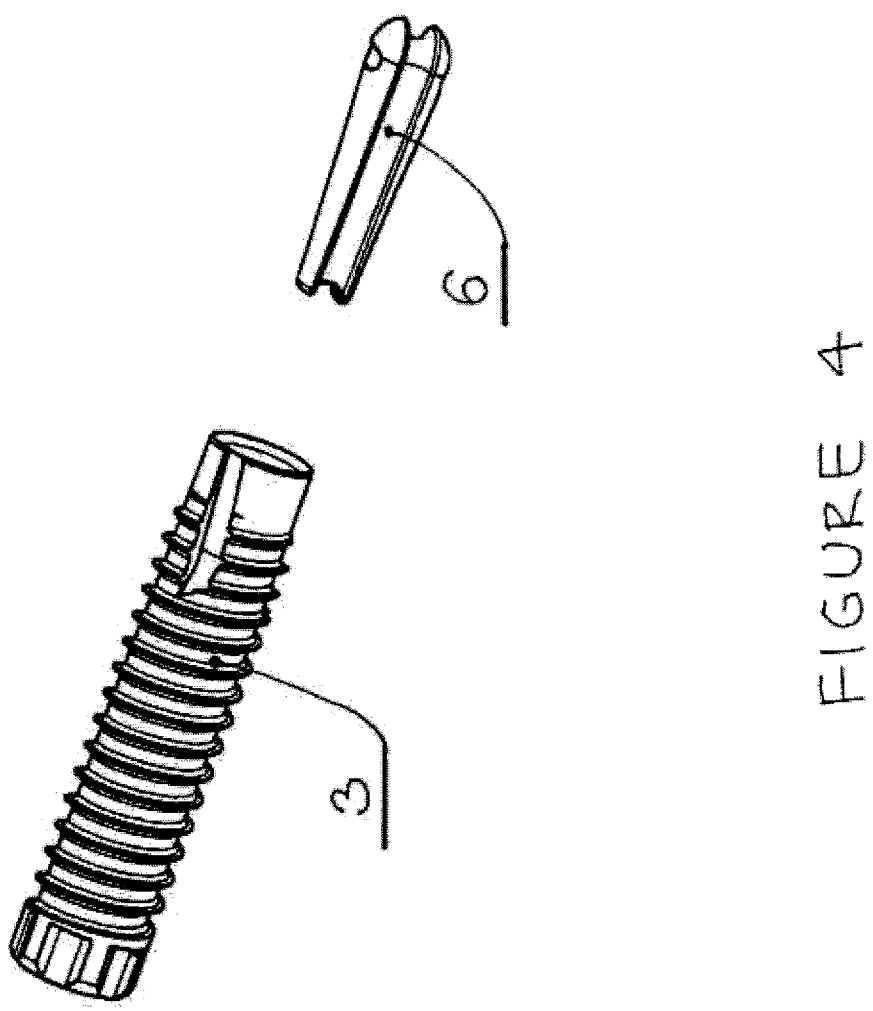

FIG. 4 A perspective view of a bone anchor and a grooved peg.

Figure 5:
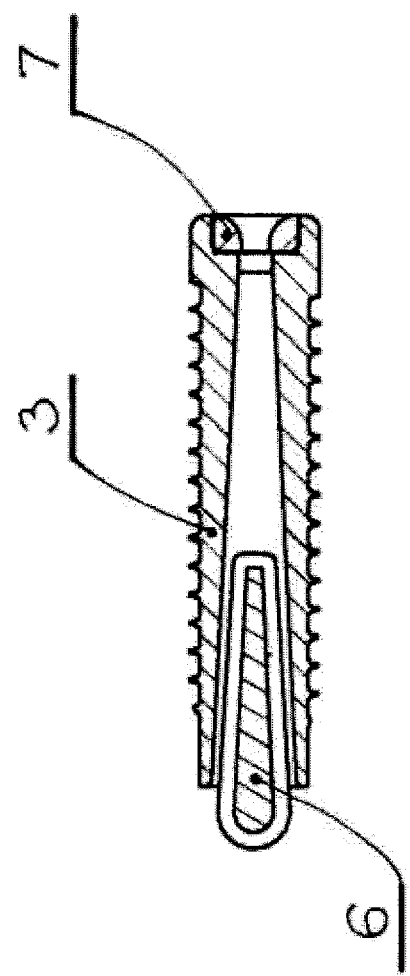

FIG. 5 A cross sectional view of a bone anchor with an eyelet on one end and a grooved peg on the other end.

Figure 6:
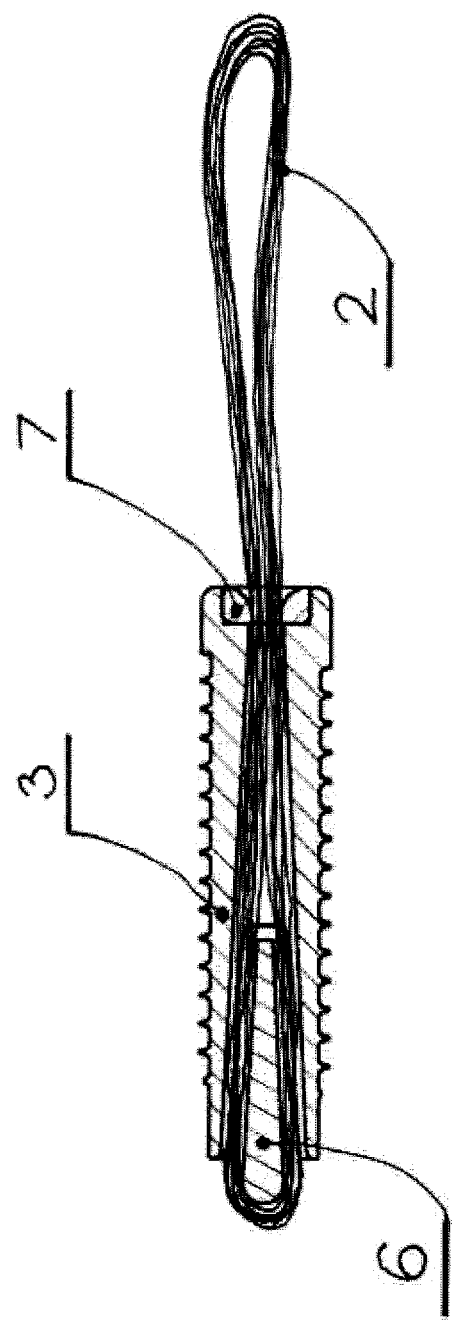

FIG. 6 A cross sectional view of a bone anchor and a closed suture loop.

Figure 7:
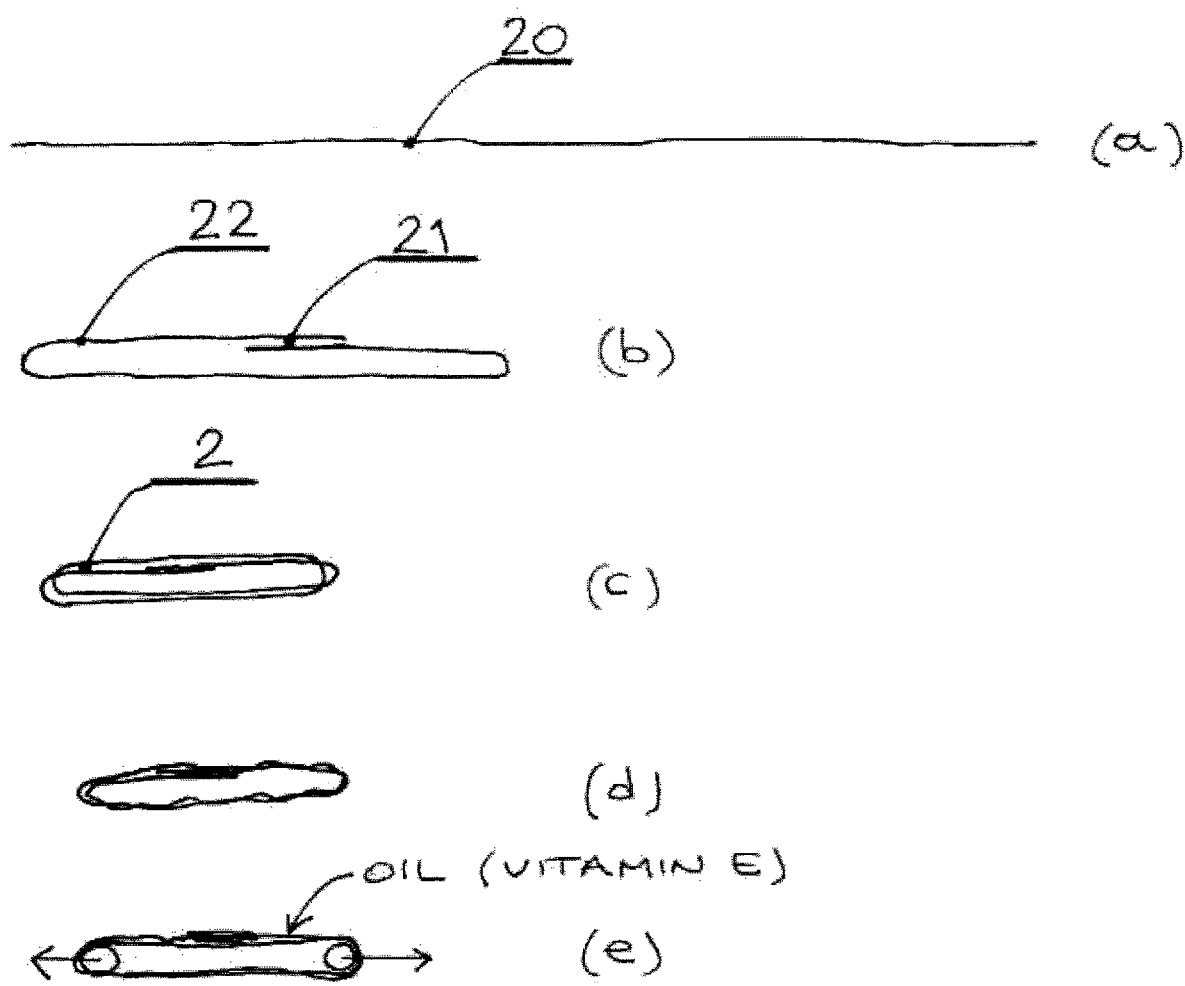

FIG. 7 A scheme of a production process of a closed suture loop.

Figure 8:
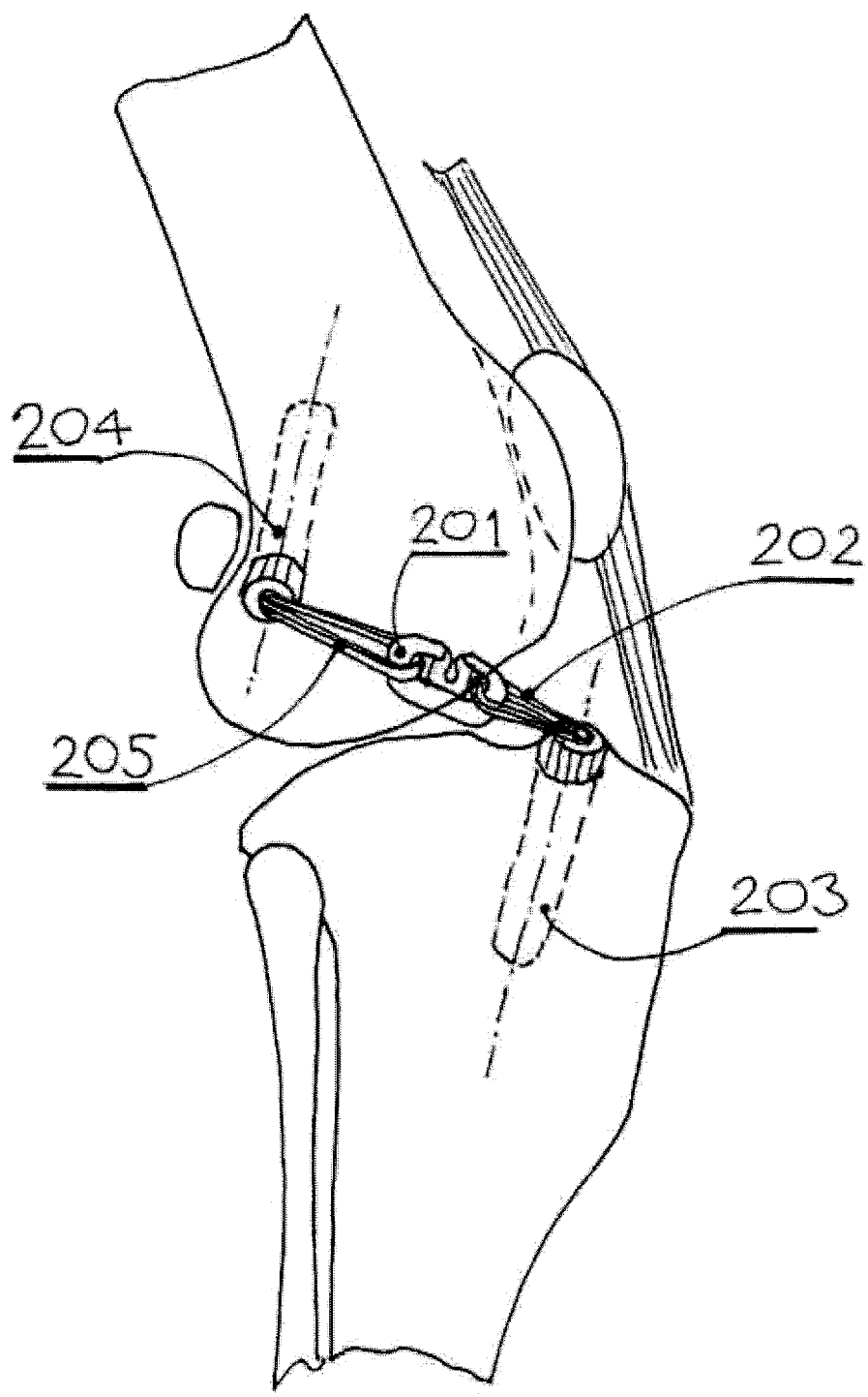

FIG. 8 An assembly applied to the lateral side of a canine knee.

Figure 9:
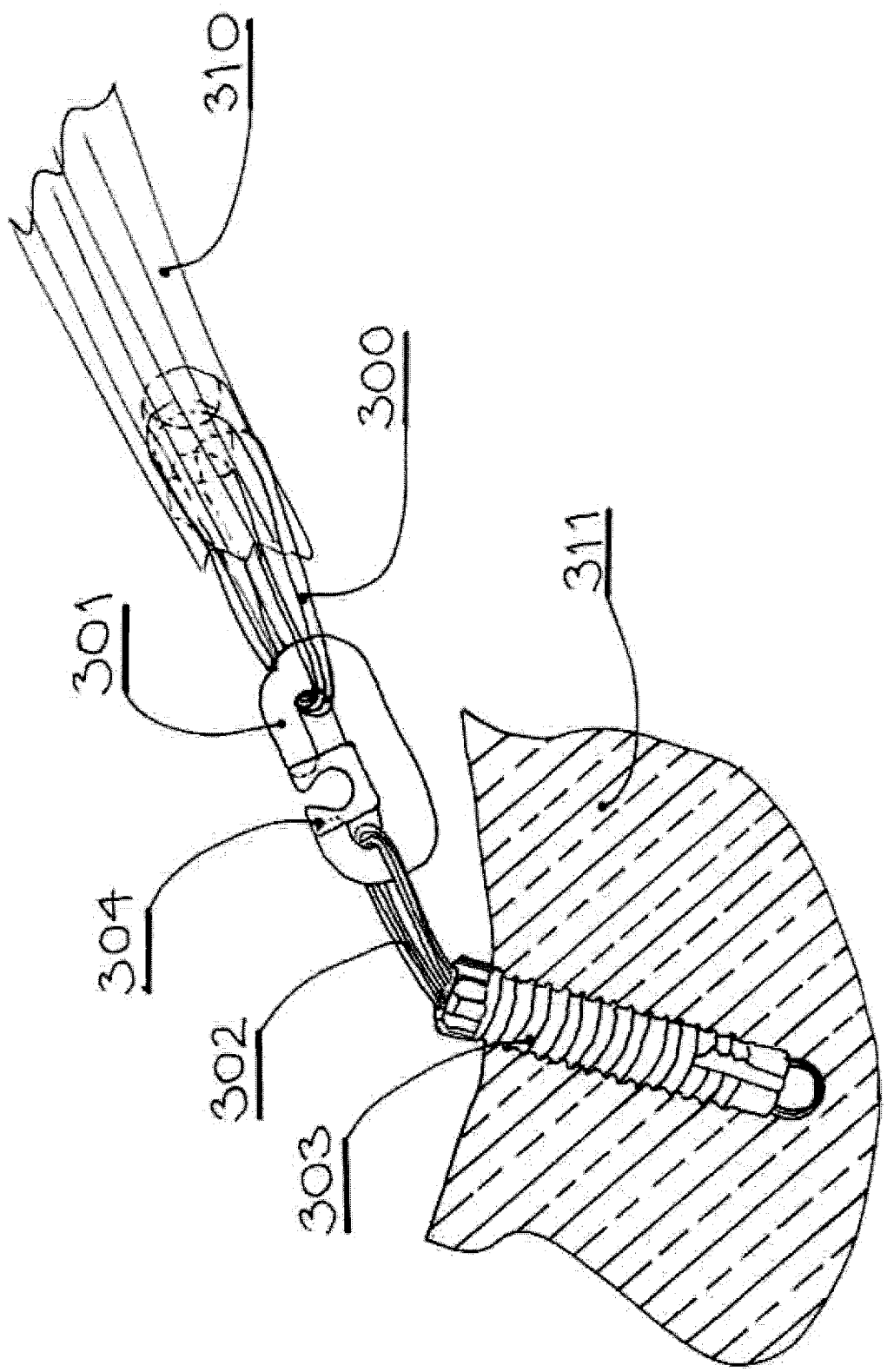

FIG. 9 An anchor/suture/link construct for affixing a ruptured tendon to bone.

DETAILED DESCRIPTION OF PREFERRED EMBODIMENTS

FIG. 1 shows the assembly 100 according to the invention with a link 1 connecting two suture loops 2 and 2a. The suture loops 2 and 2a are fixed within two bone anchors 3 and 3a by wrapping them around two conical, grooved pegs 6 and 6a. Suture loops are secured in the link 1 by a link lock 4, snapped into the link opening 5 after the link is hooked into the suture loops 2 and 2a. Bone anchors exit ends are provided by ruby eyelets 7 and 7a. Free lengths 102 and 104 of the suture loops plus the length 103 of the link add up to the desired total length 105 of the construct between the two bone anchors. Preferred material for the suture loops 2 is highly oriented ultra-high molecular weight polyethylene (UHMWPE), e.g. Dyneema Purity®, from DSM, but other high strength polymeric fibers can also be successfully used. The bone anchors 3 are preferably made from biocompatible metals, e.g. titanium or titanium alloys, stainless steels, cobalt-chromium alloys, but ceramics, including mono-crystalline ceramics, can also be utilized. Eyelets 7 are best performing when made from mono-crystalline ceramics, such as ruby, but poly-crystalline ceramics are a good alternative. If ceramics are used for the bone anchors, the eyelets can be made as integral parts of the body of the anchors. To allow for variable lengths of the total length 105 needed in surgical application, the suture loops, pre-assembled with the bone anchors, are manufactured in length increments of for example 2 mm. For the final adjustment, the links can be made in even finer length increments, for example in 1 mm. The system may then comprise of the loops/anchors available in length increments from the shortest, e.g. 6 mm, to the longest, in 2 mm increments, while the link is provided in its basic length, e.g. 9 mm, with two additional lengths, e.g. 8 mm and 10 mm. All implants are preferably supplied sterile-packaged.

FIG. 2a shows the link lock 4; FIG. 2b the link 1 of the length 103 with an opening 5; and FIG. 2c the link lock 4 and the link 1 snapped together. While the strength requirement on the link 1 calls for use of high strength materials, such as stainless steel, titanium, titanium alloys, cobalt-chromium alloys, zirconium alloys, ceramics or mono-crystalline ceramics, the link lock 4 needs some elasticity for it is to be snap-fitted into the opening 5. Preferred materials for the link lock are thus polymers, such as polyamide (PA), polypropylene (PP), polyoxymethylene (POM), or, most preferably, polyether-ether-ketone (PEEK) for its biocompatibility, stability and strength.

FIG. 3 is a perspective view of the link 1 with a link lock 4 snapped in place.

FIG. 4 is a perspective view of the bone anchor 3 rear end with a conical, grooved peg 6. The suture loop is wrapped around the grooved peg. When the suture is passed through the bone anchor and the peg pulled into the conical recess of the bone anchor, the strength of the anchorage can consistently approach the strength of the suture loop.

FIG. 5 is a cross sectional view of the bone anchor 3 and the grooved peg 6 inserted into the conical recess of the anchor in its rear end. The exit end of the bone anchor is provided by an eyelet 7, preferably press-fitted into the recess of the bone anchor.

FIG. 6 shows a cross sectional view of the closed suture loop 2, assembled with the bone anchor 3. The section of the suture loop that wraps around the grooved peg should be carefully chosen to include the spliced zone of the yarn (see FIG. 7). When placed into the confined section of the groove and the conical recess of the bone anchor, the splice is prevented from disentangling. Mechanical testing did not show the risk of failure at the splice to be any higher than at any other section of the suture loop. By contrast, if the splice is located within a free section of the loop, the strength loss can be up to 50%.

FIG. 7 illustrates the process of the suture loop production from the yarn. An appropriate, measured length of the yarn, 20, shown on FIG. 7a, is made into a closed loop 22 of the single yarn by e.g. air-splicing at the zone 21, shown on FIG. 7b. Alternatively, a knot could be tied to create the loop 22. Multiple folding of the loop 22 gives the final loop 2, FIG. 7c. In the current application as a lateral extracapsular suture for cranial cruciate rupture in medium sized dogs, we are using a 440 dtex Dyneema yarn, 6 times folded, resulting in 12 yarn strands leaving the bone anchor through a 1 mm diameter ruby eyelet. Tensile static strength is in excess of 1'000 N. After folding, the suture loop 2 can be optionally twisted between its ends, FIG. 7d, before being placed under tension and fused. Fusion process of similar materials for fishing lines is described in e.g. U.S. Pat. No. 6,148,597. Mineral oil disclosed in U.S. Pat. No. 6,148,597 as a facilitating agent in fusion process, we have replaced for this medical application by α-tocopherol, a form of vitamin E. We have tested fusion temperature in the preferred range of 147° to 153° C., with 149° to 151° C. for 15 to 30 minutes finally chosen for the production.

FIG. 8 illustrates the use of the invention for the lateral extracapsular suture in dogs with ruptured cranial cruciate ligaments. An anchor 203 is inserted into the lateral, cranial aspect of the tibia, starting at the position of the tuber of Gerdy, aimed medially and distally along the shaft of the tibia at about 45 degrees from the saggital plane of the bone. Suture loop 202 on the tibia side is usually chosen to be the shortest one available—in the current system 8 mm. An anchor 204 is inserted into the femur, just cranial and distal to the tibio-fabellar joint. It is directed proximally and cranially towards the mid-point of the femur shaft, somewhat proximally to the proximal end of the patellar groove. The anchors do not penetrate the medial cortex. The length of the suture loop 205 on the femoral side is chosen by measuring the total distance between the insertion points and subtracting the loop length of the tibia side and the length of the planned link 201.

While this is the most common anticipated use of the invention, there are many other potential applications in animals and in humans. Placing one such suture on the lateral side as described and a second one approximately parallel to the caudal suture, but on the medial side of the joint, would resolve the instability in rare cases where both cruciates are ruptured. High strength of the construct with relatively small bone anchors is of particular advantage for use in humans, where two crossing implants can be accommodated on the same side of the joint, both medially and laterally. Placement of such a system between the patella and the femur in humans is also possible, as well as at many other joints, e.g. shoulder, elbow, ankle and spine.

A link 301 and its link lock 304 according to this invention can also facilitate attachment of multiple strands 300 of a suture connecting a torn tendon 310 to the bone anchor 303 with its loop 302, fixed in bone 311, as illustrated in FIG. 9.

The invention claimed is:

1. A construct comprising two bone anchor elements in which a respective one of two closed suture loops is fixed, an open link hook with an opening configured to receive each closed suture loop, and a link lock configured to snap fit in the opening of the link hook, wherein said closed suture loops comprise fibers.

2. The construct implant according to claim 1, which the link hook is provided in several lengths.

3. The construct according to claim 1, which the link hook is produced from biocompatible metal or ceramic materials such as stainless steel, titanium, titanium alloys, cobalt-chromium alloys, zirconium alloys, ceramics or monocrystalline ceramics.

4. The construct according to claim 1, wherein the anchor element and the closed suture loop are pre-assembled into a loop-anchor implant with pre-set free lengths of the closed suture loop.

5. The construct according to claim 4, wherein the loop-anchor implant comprises a grooved peg inserted within an opening of the anchor element, wherein grooves of the grooved peg receive the anchored end of the closed suture loop.

6. The construct according to claim 5, wherein a portion of the closed suture loop is exterior to the grooved peg and the anchor element, wherein said portion of the closed suture loop is flush with the grooved peg.

7. The construct according to claim 1, wherein the anchor element is provided with an abrasion reducing eyelet.

8. The construct according to claim 1, wherein the closed suture loop is produced from a high-strength, highly oriented ultra-high molecular weight polyethylene.

9. The construct according to claim 8, wherein the closed suture loop is produced by multiple folding of a loop produced from a single yarn length, air-spliced or tied end-to-end to close the loop.

10. The construct according to claim 1, wherein the fibers of each closed suture loop are fused together at temperatures above 140° C.

11. The construct according to claim 1, wherein the free lengths of the two closed suture loops plus the length of the open link hook adding to a total linkage length, matching the desired distance between the anchor points of the two anchor elements.

12. A construct comprising an open link hook and a bone anchor element in which a closed suture loop is fixed, wherein the closed suture loop is adapted to be hooked into an opening of the open link hook, and a link lock configured to snap fit in the opening of the link hook, wherein the construct is adapted to affix a torn tendon to bone to which the bone anchor element is anchored by means of multiple strands of a suture sewn to the tendon and hooked into the link hook.

* * * * *